(12) United States Patent
Lau et al.

(10) Patent No.: US 10,030,108 B1
(45) Date of Patent: Jul. 24, 2018

(54) INITIATOR OR LINKER FREE FUNCTIONALIZATION OF POLYETHYLENE RESIN WITH ANTIMICROBIAL PROPERTY AND METHODS OF FABRICATION THEREOF

(71) Applicant: Ka Shui Manufactory Co. Ltd., Hong Kong (HK)

(72) Inventors: Yiu Ting Richard Lau, Hong Kong (HK); Wenjun Meng, Hong Kong (HK); Luchi Lin, Hong Kong (HK); Sau Kuen Connie Kwok, Hong Kong (HK); Wai Chung Wong, Hong Kong (HK); Cheuk Nang Sung, Hong Kong (HK)

(73) Assignee: Ka Shui Manufactory Co. Ltd., Hong Kong (HK)

( * ) Notice: Subject to any disclaimer, the term of this patent is extended or adjusted under 35 U.S.C. 154(b) by 0 days.

(21) Appl. No.: 15/456,854

(22) Filed: Mar. 13, 2017

(51) Int. Cl.
| | |
|---|---|
| *C08F 2/46* | (2006.01) |
| *C08F 2/50* | (2006.01) |
| *C08G 61/04* | (2006.01) |
| *C08J 3/28* | (2006.01) |
| *A01N 43/08* | (2006.01) |
| *A01N 25/10* | (2006.01) |
| *B29B 7/08* | (2006.01) |
| *B29B 13/08* | (2006.01) |
| *B29B 9/12* | (2006.01) |
| *B29B 9/06* | (2006.01) |
| *B29B 13/02* | (2006.01) |
| *B29C 67/24* | (2006.01) |
| *B29K 23/00* | (2006.01) |
| *B29K 105/00* | (2006.01) |

(52) U.S. Cl.
CPC ............... *C08J 3/28* (2013.01); *A01N 25/10* (2013.01); *A01N 43/08* (2013.01); *B29B 7/08* (2013.01); *B29B 9/06* (2013.01); *B29B 9/12* (2013.01); *B29B 13/021* (2013.01); *B29B 13/08* (2013.01); *B29C 67/24* (2013.01); *B29K 2023/065* (2013.01); *B29K 2023/0625* (2013.01); *B29K 2023/0633* (2013.01); *B29K 2105/0011* (2013.01); *B29K 2105/251* (2013.01); *C08J 2323/26* (2013.01)

(58) Field of Classification Search
USPC .......................... 522/130, 129, 113, 1; 520/1
See application file for complete search history.

(56) References Cited

U.S. PATENT DOCUMENTS

| | | | |
|---|---|---|---|
| 4,737,391 A | 4/1988 | Lustig et al. | |
| 5,055,328 A | 10/1991 | Evert et al. | |
| 8,927,616 B2 * | 1/2015 | Thomas | ................... A61L 27/16 522/126 |
| 2006/0177489 A1 * | 8/2006 | Massouda | ............... A61L 15/28 424/443 |
| 2007/0104901 A1 | 5/2007 | Siegel et al. | |
| 2011/0116992 A1 * | 5/2011 | North | ...................... B29C 59/14 422/503 |

FOREIGN PATENT DOCUMENTS

WO 2016110271 A1 7/2016

* cited by examiner

*Primary Examiner* — Jessica Whiteley
(74) *Attorney, Agent, or Firm* — Spruson & Ferguson (Hong Kong) Limited

(57) ABSTRACT

The present invention generally relates to a thermoplastic resin which is functionalized by an initiator- or linker-free process and imparted with functional properties, and related methods of fabrication. In particular, the present invention relates to methods of covalently modifying the thermoplastic resin using plasma before or after being introduced with an active agent having said functional properties.

12 Claims, 7 Drawing Sheets

|  | #1 | #2 |
|---|---|---|
| LDPE (control) |  $4.01 \times 10^1$ |  $4.01 \times 10^1$ |
| LDPE-p-Tween20 |  0 |  0 |

|  | #1 | #2 | Avg. |
|---|---|---|---|
| LDPE (control) |  |  | |
| | $2.73 \times 10^4$ | $9.65 \times 10^3$ | $1.85 \times 10^4$ |
| L1: p-LDPE-Tween20 |  |  | |
| | $8.07 \times 10^1$ | $4.04 \times 10^2$ | $2.42 \times 10^2$ |
| L2: p-LDPE-chitosan |  |  | |
| | $1.41 \times 10^2$ | $1.41 \times 10^2$ | $1.41 \times 10^2$ |
| L3: p-LDPE-Tween20-chitosan |  |  | |
| | $1.21 \times 10^2$ | $3.23 \times 10^2$ | $2.22 \times 10^2$ |

INITIATOR OR LINKER FREE FUNCTIONALIZATION OF POLYETHYLENE RESIN WITH ANTIMICROBIAL PROPERTY AND METHODS OF FABRICATION THEREOF

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to a thermoplastic resin which is functionalized by an initiator- or linker-free process and imparted with functional properties, and related methods of fabrication. In particular, the present invention relates to methods of covalently modifying the thermoplastic resin using plasma before or after being introduced with an active agent having said functional properties.

BACKGROUND

Functionalization of thermoplastic resin to gain certain functional properties by chemical or irradiation method is well known in the art. For instance, corona treatment including plasma to treat surface of thermoplastic polymer is commonly used.

In US20060177489A1, a method for attaching a chitosan to the surface of the polymers that includes at least one rehydration step to provide more effective and stable chitosan coating was provided. The articles made with those polymers provide antibacterial and anti-odor properties. Plasma treatment as one of the treatments for pre-treating the surface of the polymers to acquire a wettable surface before chitosan coating was described in that patent.

US20070104901A1 also described that an important use of irradiative treatments including plasma on polymer sheets and films is to induce cross-linking between molecules of the irradiated material. It also cited some older US patents such as U.S. Pat. No. 4,737,391 and U.S. Pat. No. 5,055,328, which disclosed different irradiation methods to treat polymer surface.

However, there is no literature teaching or suggesting using plasma treatment to modify thermoplastic resin in order to gain certain functions from forming bonds with active agents covalently. The present invention aims to fulfill this unmet need.

SUMMARY OF THE INVENTION

Accordingly, a first aspect of the present invention is to provide a linker- or initiator-free method for covalently modifying thermoplastic resin comprising pre-treating the thermoplastic resin or a mixture containing thereof with plasma in order to introduce functional groups to the backbone of the thermoplastic resin so as to enable the functionalized thermoplastic resin to form covalent bond (or being covalently grafted) with active agents such as antimicrobial agent when they are in contact under certain reaction conditions. The method also comprises preserving the functional groups introduced by said plasma. One embodiment of said preserving the functional groups of the backbone of the thermoplastic resin is via vacuum packaging, for example, in a low-pressure oxygen environment. Another embodiment of said preserving is via dry mixing of the plasma treated thermoplastic resin with said active agents which contain reactive groups corresponding to those functional groups introduced by plasma. It is possible that both vacuum packaging and dry mixing with other agents containing reactive groups are used to preserve the functional groups of the backbone of the thermoplastic resin. It is also possible that either the thermoplastic resin is pre-treated with plasma before covalently binds with the other agents or the thermoplastic resin is mixed with the other agents to form a mixture before plasma treatment.

After said plasma treatment and preservation of functional groups, the present method further comprises melt processing the functionalized thermoplastic resin which is bound with the active agents. Said melt processing comprises one or more of wet reaction, thermal annealing, and/or extrusion. In one embodiment, after said wet reaction or thermal annealing, purification (e.g., solvent rinsing and filtration) is carried out to remove excess solvent before drying the filtrate. In an alternative embodiment, pelletization is carried out after said extrusion to form thermoplastic pellets, granules or powders. Depending on the desired shape and size of the final article, different molding techniques can be used to mold the thermoplastic pellets, granules or powders into solid, monolith, tube, composite, fiber, film, sheet and varnish, etc., after said purification or pelletization. Said molding includes but not limited to extrusion, injection molding, compression molding, blow molding, blow filming, film casting, spinning, hot pressing, and overmolding on substrates.

Preferably, in the first aspect of the present invention, the thermoplastic resin being modified by the present method includes but not limited to polyethylene (PE) resin. More preferably, said PE resin is low-density PE (LDPE), linear low-density PE (LLDPE), and high-density PE (HDPE) resin. Other polyethylene-based resins should be understood as potential candidates of said PE resins modifiable by the present method.

In one embodiment, the functional groups introduced by plasma include but not limited to TWEEN® 20. TWEEN® 20 can also serve as said active agents of the present invention since it has anti-microbial property.

In another embodiment, said active agents which contain reactive groups are selected from a charge-carrying or a neutral polymer.

In other embodiment, said active agents include but not limited to deacetylated chitosan, single-armed or multi-armed sorbitan- or sorbitol-centered linear polyethylene glycols bearing at least one active chain-compatibilizing group at one or both of the terminals of said linear polyethylene glycols. Preferably, said active agents comprise TWEEN® 20, TWEEN® 80, PEG-sorbitol hexaoleate, PE-b-PEG, and Ceteareth-20.

In yet another embodiment, said active agents are anti-microbial agents. Preferably, said anti-microbial agents comprise anti-fouling and bacteria-repellent agents.

A second aspect of the present invention relates to a thermoplastic resin covalently bound with an active agent which is produced by the method in the first aspect of the present invention. Said thermoplastic resin, because it is pre-treated with plasma before being subjected to melt processing and subsequent molding, is relatively more stable in terms of the bonding with the active agent, e.g., an anti-microbial agent, than other functionalized thermoplastic resin produced by the conventional method in the absence of plasma treatment. Said preserving step in the present method also improves the functional groups on the backbone of the thermoplastic resin introduced by plasma, increasing the efficiency of forming covalent bond with the active agent even when a relatively lower concentration of the active agent is used to react with the functionalized thermoplastic resin. In other words, the production of the thermoplastic resin can be easily scaled up because no linker or initiator (e.g., coupling agent or additives such as EVA-MA) is required but simply by using plasma treatment and corresponding preservation step(s). Production cost is thereby significantly reduced. Using a smaller amount of active agent can also reduce yellowness and minimize the level of decomposition of the thermoplastic resin during fabrication, leading to a chemically safe plastic material with wider applications such as in food packaging.

BRIEF DESCRIPTION OF THE DRAWINGS

Embodiments of the invention are described in more details hereinafter with reference to the drawings, in which.

DETAILED DESCRIPTION

In the following description, and the present method of modifying thermoplastic resin and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
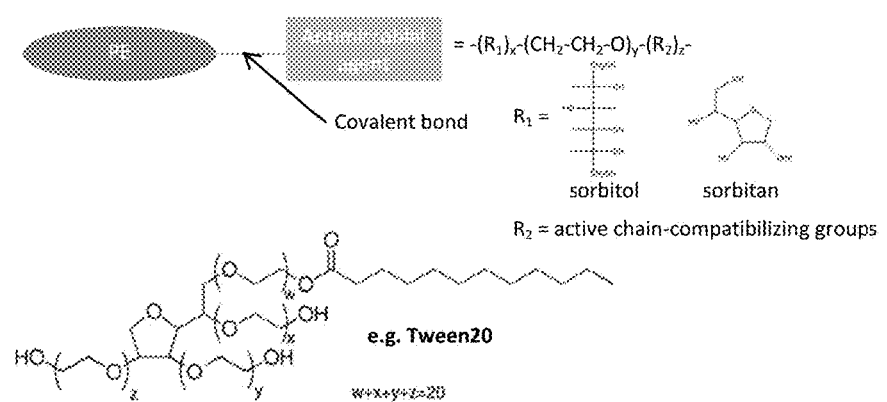
FIG. 1 is a schematic diagram showing the key components of a functionalized thermoplastic resin, polyethylene (PE), which is modified by plasma treatment to form a covalent bond with an anti-microbial agent according to an embodiment of the present invention.

FIG. 1 illustrates a basic structure of a functionalized thermoplastic resin, e.g. PE resin, which is covalently bound with an active agent, e.g. deacetylated chitosan (not shown in FIG. 1), single armed or multi-armed sorbitol- or sorbitan-centered linear PEG having active compatibilizing groups at one terminal, according to the present method. TWEEN® 20 is used in this example to be introduced into the backbone of the PE resin as functional groups under the plasma treatment. Said functional groups may correspond to those reactive groups present on the active agent such that when they bring together under certain reaction conditions, covalent bond is readily formed between the functionalized PE resin and the active agent. Other possible active agents with the desired functional properties to be imparted into the functionalized thermoplastic resin, e.g., anti-microbial property, can be bound to the functionalized thermoplastic resin modified according to the present method.

Figure 2:
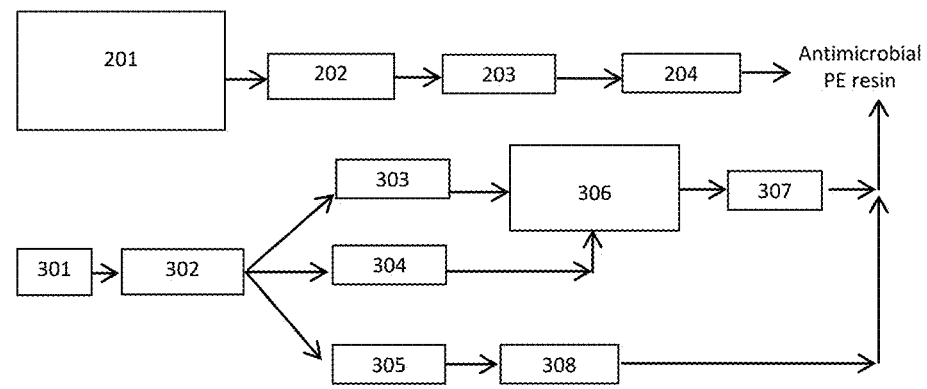
FIG. 2 illustrates in a form of flowchart two alternative implementation embodiments of the present method.

FIG. 2 shows two alternative embodiments to implement the present method. In FIG. 2, the first implementation embodiment is to pre-mix the PE resin and the anti-microbial agent (201) before being subjected to plasma treatment (202), followed by extrusion (203) and then pelletization (204). This embodiment can be carried out in a static transfer tray. Alternatively, the present method can be implemented by pre-treating the PE resin with plasma (301) before mixing with said anti-microbial agent (302). This alternative embodiment can be carried out in an RF plasma machine with a rotary drum. Depending on how to mix the pre-treated PE resin with the anti-microbial agent, the subsequent processing step can be different. Either the reaction between the pre-treated PE resin and the anti-microbial agent takes place in an aqueous solution (wet reaction) by adding the pre-treated PE granules into said aqueous solution containing the anti-microbial agent under heat (at about 54° C.) and constant stirring in a closed system for 24 hours (303), or the reaction takes place in an oven (oven treatment) where the pre-treated PE resin are mixed with the anti-microbial agent in a sealable container, e.g., a vacuum package, and heated at 54° C. for 24 hours (304), or the pre-treated PE resin and the anti-microbial agent are gently mixed before being subjected to extrusion (305). If wet reaction (303) or oven treatment (304) is employed, the reaction mixture will be subjected to purification (306), e.g., solvent rinsing and filtration, followed by drying at 37° C. for 2 days (307), in order to remove excess solution and/or unreacted agents. If extrusion (305) is employed, the pre-treated PE resin and the anti-microbial agent are melt-processed in a single-screw or twin-screw extruder followed by pelletization (308). The pellet, powder, or granules after said drying (308) or said pelletization (308) can be further processed such as injection molding or hot pressing in order to produce an article with desired shape, size and dimension.

Example 1

Figure 3:
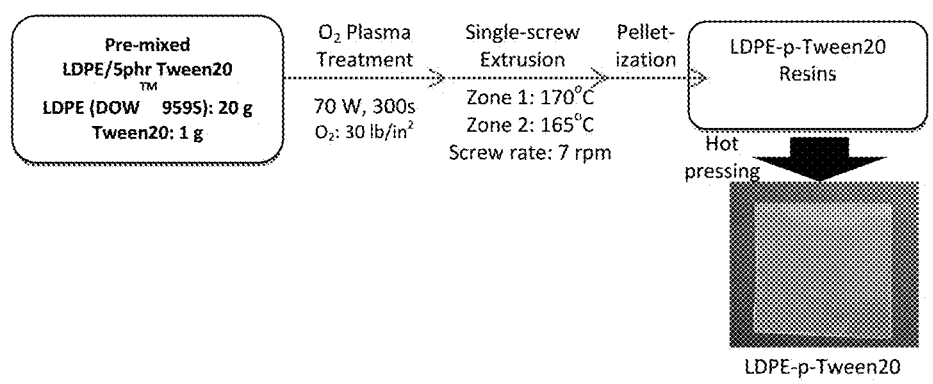
FIG. 3 is a more detailed flowchart illustrating an embodiment of the present method.
Figure 5:
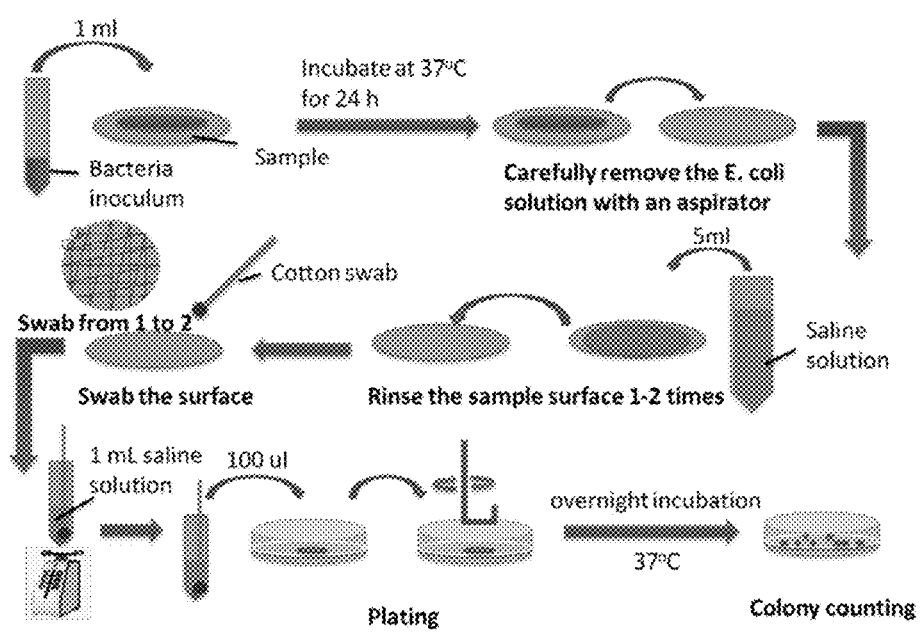
FIG. 5 is a schematic diagram illustrating procedures of a bacteria repellency test for different samples of thermoplastic resin produced according to certain embodiments of the present invention.
Figure 6:
FIG. 6 shows the bacteria repellency test result of one group of samples of thermoplastic resin produced by one of the two alternative embodiments of the present method.
Figure 6:
Figure 6:
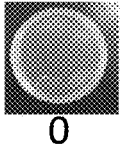
Figure 6:

FIG. 3 illustrates a specific example which uses LDPE (DOW™ 959S) resin as the thermoplastic resin to pre-mix with TWEEN® 20 as the anti-microbial agent before being subjected to plasma treatment. In this example, the dry weight ratio between LDPE resin and TWEEN® 20 is 20:1, i.e., 20 g LDPE resin is pre-mixed with 1 g TWEEN® 20. To preserve the functional groups introduced by plasma into the backbone of the LDPE resin, plasma treatment is carried out under nearly vacuum environment (e.g., 30 lb/in$^2$ oxygen). The plasma power and duration are set at 70 W and 300 seconds, respectively, in this example. The plasma-treated LDPE-TWEEN® 20 conjugates are subjected to extrusion in a single-screw extruder having two temperature zones (Zone 1 and Zone 2) set at 170° C. and 165° C., respectively, and with a screw rate of 7 rpm. The single-screw extruder may be equipped with a pelletizer or the extruded samples can be further subjected to an external pelletizer to carry out pelletization. Pellets formed after said pelletization can be further subjected to hot pressing in order to reform the anti-microbial PE resin pellet into a sheet. The resulting sheet is further subjected to bacteria repellency test. Detail procedures of how to perform the bacteria repellency test are illustrated in FIG. 5. The bacteria repellency test result of the resulting sheet from this example (labeled as "LDPE-p-Tween 20" in FIG. 3 and FIG. 6) as compared to a control (i.e., LDPE only without any plasma treatment and TWEEN® 20) is shown in FIG. 6.

Example 2

Figure 4:
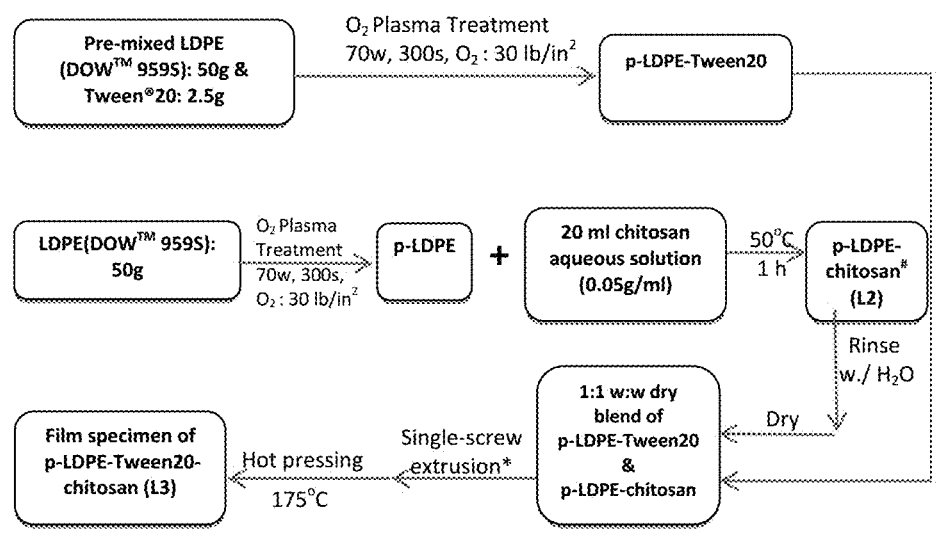
FIG. 4 is a more detailed flowchart illustrating another embodiment of the present method.
Figure 7:
FIG. 7 shows the bacteria repellency test result of one group of samples of thermoplastic resin produced by another one of the two alternative embodiments of the present method.
Figure 7:
Figure 7:
Figure 7:
Figure 7:
Figure 7:
Figure 7:
Figure 7:

FIG. 4 shows another example of using LDPE resin to pre-mix with TWEEN® 20 followed by plasma treatment with the same plasma conditions used in Example 1 to obtain a LDPE-TWEEN® 20 conjugate and the film specimen made of this conjugate (also labeled as "p-LDPE-Tween 20" or "L1" in FIG. 4 and FIG. 7), while 20 mL of deacetylated chitosan at 0.05 g/mL (i.e., 1 g chitosan) is mixed with 50 g plasma-treated LDPE resin followed by extrusion and subsequently hot pressing at 50° C. for 1 hour to obtain a LDPE-chitosan conjugate and the film specimen made of this conjugate (also labeled as "p-LDPE-chitosan" or "L2" in FIG. 4 and FIG. 7). This conjugate L2 can be further mixed with the conjugate L1 and then extruded to form another conjugate. Firstly, the conjugate L2 is rinsed with $H_2O$ and then dried at 60° C. After that, conjugates L1 and L2 are mixed in a dry weight ratio of 1:1 and then subjected to extrusion in a single-screw extruder having two temperature zones (Zone 1 and Zone 2) set at 170° C. and 165° C., respectively, followed by hot pressing at 175° C. in order to obtain a film specimen made of LDPE-TWEEN® 20-chitosan conjugate (also labeled as "p-LDPE-Tween 20-chitosan" or L3 in FIGS. 4 and 7). The three film samples and a control (labeled as "LDPE" in FIG. 4 and FIG. 7, which contains LDPE resin only without being subjected to plasma treatment or mixing with any active agent) are added with 1 mL of *E. coli* suspension (~$10^7$ cells/mL in 1/500 NB) as an inoculum for bacterial adsorption examination at 37° C. for 24 hours. After the 24-hour incubation, the three samples and the control are subjected to swab tests after rinses with 5 mL saline. Detailed procedures of how to conduct a bacteria repellency test are illustrated in FIG. 5. The results are shown in FIG. 7. The results suggest that the film specimen (L2) made of plasma-treated LDPE resin covalently bound with chitosan appears to be the best in terms of reduction in adsorption of *E. coli* (99.2%) among the three specimens, while the other two specimens with TWEEN® 20 have similar reduction percentages in adsorption of *E. coli* (98.7% reduction for L1 and 98.8% reduction for L3).

Example 3

An RF plasma machine (GUARDER® GDR-150-T, Shangdong) configured with a rotary drum having a size of 400(Φ)×450(L) mm and a rotating speed of 50 Hz (anticlockwise) is employed in this example. The power of the plasma is 500 W at 13.56 MHz. The plasma treatment is carried out on LDPE (DOW® 959S) under a very low oxygen environment (e.g., 200 sccm $O_2$ @ 70 Pa) for preservation of the plasma-induced functional groups on the LDPE backbone. Firstly, 2.5 kg of LDPE granules are transferred to a meshed drum in the plasma machine which is set to the operation conditions as described in this example. Secondly, a low oxygen environment is established by depressurization in the reaction chamber, followed by injecting suitable amount of oxygen into the reaction chamber at regulated pressure as described in this example, then applying suitable voltage to generate plasma, and after plasma treatment for certain period of time, the remaining oxygen is vented out from the reaction chamber. The plasma-treated LDPE granules are then transferred onto a paper board tray to avoid any contact by bare hands. 25 mL of TWEEN® 20 is mixed evenly with 2.5 kg plasma-treated LDPE granules (resulting in 1% (v/w) TWEEN® 20), or 250 ml of TWEEN® 20 is mixed evenly with 2.5 kg plasma-treated LDPE granules (resulting in 10% (v/w) TWEEN® 20) in a sealable bag by vigorous shaking and rotating driven by the rotary drum at the rotating speed as described in this example. Based on the plasma conditions described in this example, different samples are prepared according to different plasma treatment time durations (from 3 minutes to 15 minutes in this example) and with/without the subsequent mixing with the active agent (TWEEN® 20 in this example). Table 1 below lists the corresponding plasma time duration and active agent concentration for each of the samples:

TABLE 1

| Sample No. | Duration (min) | Input of LDPE (kg) | Output of LDPE (kg) | % (v/w) of TWEEN ® 20 to be added after plasma |
|---|---|---|---|---|
| #1 | 15 | 1.0 | 1.0 | 1 |
| #2 | 15 | 2.5 | 2.5 | 1 |
| #3 | 10 | 2.5 | 2.5 | 1 |
| #4 | 5 | 2.5 | 2.5 | 1 |
| #5 | 3 | 2.5 | 2.5 | 1 |
| #6 | 5 | 2.5 | 2.5 | Nil |
| #7 | 5 | 2.5 | 2.5 | Nil |
| #8 | 5 | 2.5 | 2.5 | 10 |
| #9 | 5 | 2.5 | 2.5 | 10 |
| #10* | 15 | 4.0 | 3.0 | 10 |
| #11* | 15 | 4.0 | 1.0 | 5 |

*Samples #10 and #11 are from the same batch (4 kg) of plasma treatment. 3 kg were taken to do the corresponding grafting treatment to be #10, while 1 kg was taken separately to do another corresponding grafting treatment to be #11 batch.

Each of the above samples in Table 1 is further processed by the three different ways, i.e., (a) wet reaction, (b) extrusion, and (c) oven treatment. Table 2 below lists the sample name for each of the samples after different further processing steps:

TABLE 2

| | (a) Wet Reaction (54° C., 24 hrs) | | | (b) Extrusion | | | (c) Oven Treatment (54° C., 24 hrs, in sealer bag) | | |
|---|---|---|---|---|---|---|---|---|---|
| Sample No.* | Date of Treatment | Injection molding? | New Sample Name | Date of Treatment | Injection molding? | New Sample Name | Date of Treatment | Injection molding? | New Sample Name |
| #1 | 1 Sep. 2016 | Yes | 1a | | | | | | |
| #2 | 6 Sep. 2016 | Yes | 2a | 6 Sep. 2016 | Yes | 2b | 5 Sep. 2016 | Yes | 2c |
| #3 | 13 Sep. 2016 | Yes | 3a | 12 Sep. 2016 | Yes | 3b | 6 Sep. 2016 | Yes | 3c |
| #4 | 12 Sep. 2016 | Yes | 4a | 12 Sep. 2016 | Yes | 4b | 6 Sep. 2016 | Yes | 4c |
| #5 | 13 Sep. 2016 | Yes | 5a | 12 Sep. 2016 | Yes | 5b | 6 Sep. 2016 | Yes | 5c |
| #6 | 30 Aug. 2016 | Yes | 6a | 30 Aug. 2016 | Yes | 6b | | | |
| #7 | | | | (via liquid | | | | | |

TABLE 2-continued

| | (a) Wet Reaction (54° C., 24 hrs) | | | (b) Extrusion | | | (c) Oven Treatment (54° C., 24 hrs, in sealer bag) | | |
|---|---|---|---|---|---|---|---|---|---|
| Sample No.* | Date of Treatment | Injection molding? | New Sample Name | Date of Treatment | Injection molding? | New Sample Name | Date of Treatment | Injection molding? | New Sample Name |
| #8 | 6 Sep. 2016 | Yes | 8a | feeder) 6 Sep. 2016 | No | 8b | | | |
| #9 | | | | | | | | | |
| #10 | 1 Sep. 2016 | Yes | 10a | 7 Sep. 2016 | No | 10b | | | |
| #11 | 12 Sep. 2016 | Yes | 11a | 12 Sep. 2016 | — | 11b | | | |

*LDPE grafted with TWEEN® 20 after plasma treatment on 22 Aug. 2016 (except samples #6 and #7, which are LDPE only without TWEEN® 20)

TABLE 3

Bacteria Repellency Test Using *E. coli*

| Sample Name | $1^{st}$ | $2^{nd}$ | $3^{rd}$ | Average | Reduction % |
|---|---|---|---|---|---|
| Control (sample #6) | $8.63 \times 10^4$ | $3.14 \times 10^4$ | $6.99 \times 10^3$ | $4.16 \times 10^4$ | |
| 1a | $7.83 \times 10^3$ | $1.11 \times 10^3$ | $2.59 \times 10^3$ | $3.84 \times 10^3$ | 90% |
| 2a | $4.02 \times 10^2$ | $6.02 \times 10^3$ | $8.26 \times 10^3$ | $4.89 \times 10^3$ | 88% |
| 2b | $1.41 \times 10^2$ | $6.68 \times 10^3$ | $6.03 \times 10^2$ | $2.47 \times 10^3$ | 94% |
| 2c | $2.01 \times 10^2$ | $5.43 \times 10^2$ | $4.83 \times 10^2$ | $4.09 \times 10^2$ | 99% |
| 3a | $3.62 \times 10^2$ | $8.91 \times 10^3$ | $1.07 \times 10^3$ | $3.45 \times 10^3$ | 91% |
| 3b | $3.79 \times 10^4$ | $9.11 \times 10^4$ | $2.75 \times 10^4$ | $5.22 \times 10^4$ | No |
| 3c | $7.44 \times 10^2$ | $6.64 \times 10^2$ | $1.41 \times 10^3$ | $9.39 \times 10^2$ | 97% |
| 4a | $4.99 \times 10^4$ | $6.68 \times 10^3$ | | $2.83 \times 10^4$ | 31% |
| 4b | $8.56 \times 10^3$ | $2.40 \times 10^4$ | $1.14 \times 10^4$ | $1.47 \times 10^4$ | 64% |
| 4c | $2.09 \times 10^4$ | $1.14 \times 10^4$ | $5.96 \times 10^3$ | $1.28 \times 10^4$ | 69% |
| 5a | $9.46 \times 10^3$ | $6.46 \times 10^3$ | $5.23 \times 10^2$ | $5.48 \times 10^3$ | 86% |
| 5b | $1.05 \times 10^4$ | $5.65 \times 10^3$ | $3.22 \times 10^2$ | $5.49 \times 10^3$ | 86% |
| 5c | $4.83 \times 10^2$ | $2.09 \times 10^3$ | $4.28 \times 10^4$ | $1.51 \times 10^4$ | 63% |
| 6a | $2.41 \times 10^2$ | $2.01 \times 10^1$ | $7.04 \times 10^2$ | $3.22 \times 10^2$ | 99% |
| 6b | $1.21 \times 10^3$ | $6.96 \times 10^3$ | $1.61 \times 10^4$ | $8.09 \times 10^3$ | 80% |
| 8a | $1.95 \times 10^4$ | $3.82 \times 10^2$ | $1.13 \times 10^3$ | $7.00 \times 10^3$ | 83% |
| 10a | $9.05 \times 10^2$ | $2.69 \times 10^4$ | $2.32 \times 10^4$ | $1.70 \times 10^4$ | 59% |
| 11a | $2.10 \times 10^4$ | $1.36 \times 10^4$ | $4.04 \times 10^3$ | $1.29 \times 10^4$ | 68% |

TABLE 4

Bacteria Repellency Test Using *S. aureus*

| Sample Name | $1^{st}$ | $2^{nd}$ | $3^{rd}$ | Average | Reduction % |
|---|---|---|---|---|---|
| Control (Sample #6) | $4.03 \times 10^4$ | $1.41 \times 10^4$ | $1.61 \times 10^4$ | $2.35 \times 10^4$ | |
| 1a | $1.95 \times 10^4$ | $4.57 \times 10^4$ | $2.90 \times 10^4$ | $3.14 \times 10^4$ | No |
| 2a | $1.81 \times 10^4$ | $3.40 \times 10^4$ | $4.94 \times 10^4$ | $3.38 \times 10^4$ | No |
| 2b | $1.29 \times 10^3$ | $6.03 \times 10^2$ | $4.02 \times 10^2$ | $7.65 \times 10^2$ | 96% |
| 2c | $5.33 \times 10^4$ | $4.75 \times 10^4$ | $4.94 \times 10^4$ | $5.01 \times 10^4$ | No |
| 3a | $1.35 \times 10^4$ | $2.02 \times 10^4$ | $2.61 \times 10^4$ | $1.99 \times 10^4$ | 15% |
| 3b | $2.43 \times 10^3$ | $6.03 \times 10^2$ | $5.03 \times 10^2$ | $1.18 \times 10^3$ | 94% |
| 3c | $1.83 \times 10^4$ | $3.11 \times 10^4$ | $2.26 \times 10^4$ | $2.40 \times 10^4$ | No |
| 4a | $3.30 \times 10^4$ | $2.75 \times 10^4$ | $1.42 \times 10^4$ | $2.49 \times 10^4$ | No |
| 4b | $3.40 \times 10^3$ | $3.40 \times 10^3$ | $4.02 \times 10^1$ | $2.28 \times 10^3$ | 90% |
| 4c | $2.28 \times 10^4$ | $3.79 \times 10^4$ | $3.64 \times 10^4$ | $3.24 \times 10^4$ | No |
| 5a | $5.98 \times 10^4$ | $2.38 \times 10^4$ | $5.60 \times 10^4$ | $4.65 \times 10^4$ | No |
| 5b | $4.42 \times 10^2$ | $1.09 \times 10^3$ | $1.41 \times 10^2$ | $5.58 \times 10^2$ | 97% |
| 5c | $3.97 \times 10^4$ | $5.78 \times 10^4$ | $5.17 \times 10^4$ | $4.97 \times 10^4$ | No |
| 6a | $3.16 \times 10^4$ | $2.23 \times 10^4$ | $4.18 \times 10^4$ | $3.19 \times 10^4$ | No |
| 6b | $8.04 \times 10^2$ | $3.20 \times 10^3$ | $5.18 \times 10^3$ | $3.06 \times 10^3$ | 86% |
| 8a | $2.92 \times 10^4$ | $2.37 \times 10^4$ | $4.18 \times 10^4$ | $3.16 \times 10^4$ | No |
| 10a | $1.57 \times 10^4$ | $2.29 \times 10^4$ | $1.90 \times 10^4$ | $1.92 \times 10^4$ | 18% |
| 11a | $2.61 \times 10^4$ | $9.50 \times 10^4$ | $3.13 \times 10^4$ | $5.08 \times 10^4$ | No |

The samples that have been subjected to injection molding are further tested by the bacteria repellency according to the procedures illustrated in FIG. 5. In this example, both *E. coli* and *S. aureus* are used to swab on the injected molded samples. The results are listed in Table 3 and Table 4, respectively. Sample #6 in Table 1 (LDPE only) is taken as a control in the bacteria repellency test. Each sample is tested in triplicates.

From the above results in Table 3, the three further processes after plasma treatment, i.e., wet reaction, extrusion, and oven treatment, do not cause significant difference in the average reduction percentage of *E. coli* growth among different samples. However, it appears that the samples further processed by extrusion after plasma treatment have better average reduction percentage of *S. aureus* growth (at least 86% reduction) than those further processed by wet reaction or oven treatment. Overall, the samples added with relatively lower concentration of TWEEN® 20, e.g., 25 mL of TWEEN® 20 in 2.5 kg LDPE (sample number 2b), than the others are better in overall performance in terms of the reduction percentage of bacterial growth in both bacterial strains.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A linker-free or initiator-free method for fabricating a functionalized thermoplastic resin being covalently bound with a bacteria repellent agent, said method comprising plasma treating the thermoplastic resin before or after mixing with said bacteria repellent agent, and preserving functional groups introduced by said plasma into the backbone of said thermoplastic resin, in order to obtain a covalently grafted conjugate of plasma-treated thermoplastic resin with said bacteria repellent agent.

2. The method of claim 1, wherein said thermoplastic resin comprises polyethylene (PE) resin.

3. The method of claim 1, wherein said thermoplastic resin comprises low-density PE (LDPE), linear low-density PE (LLDPE), high-density PE (HDPE), and other polyethylene-based resins.

4. The method of claim 1, wherein said bacteria repellent agents comprise polyethylene glycol sorbitan monolaurate, polyethylene glycol sorbitan monooleate, poly(ethylene glycol) sorbitol hexaoleate, polyethene-block-poly(ethylene glycol), and alkyl polyglycol ether C16-C18.

5. The method of claim 1, wherein said bacteria repellent agent comprises polyethylene glycol sorbitan monolaurate which also introduces functional groups into the backbone of the thermoplastic resin under said plasma treatment.

6. The method of claim 1, wherein said bacteria repellent agent contains reactive groups corresponding to the functional groups introduced by said plasma.

7. The method of claim 1, wherein said preserving is via vacuum packaging, or dry mixing of said thermoplastic resin with said bacteria repellent agent which contains reactive groups corresponding to the functional groups introduced by said plasma, or both of said vacuum packaging and said dry mixing.

8. The method of claim 7, wherein said vacuum packaging is carried out in a low oxygen environment and in a sealable container when the thermoplastic resin is mixed with said bacteria repellent agent.

9. The method of claim 8, wherein said low oxygen environment is established by depressurization in a reaction chamber of a plasma machine, followed by injecting suitable amount of oxygen into the reaction chamber at a regulated pressure, then applying suitable voltage to generate plasma, and after plasma treatment for certain period of time, the remaining oxygen is vented out from the reaction chamber.

10. The method of claim 9, wherein said thermoplastic resin is transferred to a meshed drum with a rotating speed of 50 Hz, followed by establishing said low oxygen environment, then plasma treating said thermoplastic resin, and mixing plasma-treated thermoplastic resin with said bacteria repellent agent under said low oxygen environment by vigorous shaking and rotating driven by said drum.

11. The method of claim 2, wherein said bacteria repellent agent is polyethylene glycol sorbitan monolaurate, wherein the concentration of polyethylene glycol sorbitan monolaurate is 1% (v/w).

12. The method of claim 11, further comprising the step of processing the thermoplastic resin by extrusion after plasma treatment.

\* \* \* \* \*